US010957431B2

(12) United States Patent
Bao et al.

(10) Patent No.: US 10,957,431 B2
(45) Date of Patent: Mar. 23, 2021

(54) HUMAN RESOURCE SELECTION BASED ON READABILITY OF UNSTRUCTURED TEXT WITHIN AN INDIVIDUAL CASE SAFETY REPORT (ICSR) AND CONFIDENCE OF THE ICSR

(71) Applicant: International Business Machines Corporation, Armonk, NY (US)

(72) Inventors: Sheng Hua Bao, San Jose, CA (US); Pathirage Perera, San Jose, CA (US); Cartic Ramakrishnan, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 203 days.

(21) Appl. No.: 15/958,023

(22) Filed: Apr. 20, 2018

(65) Prior Publication Data

US 2019/0325999 A1    Oct. 24, 2019

(51) Int. Cl.
*G16H 15/00* (2018.01)
*G16H 10/60* (2018.01)

(52) U.S. Cl.
CPC ............. *G16H 15/00* (2018.01); *G16H 10/60* (2018.01)

(58) Field of Classification Search
CPC ......... G06F 16/00; G06F 40/40; G16H 15/00; G16H 50/70; G16H 10/60; G16H 70/40; G16H 10/20
USPC ............................................... 705/2–4; 704/9
See application file for complete search history.

(56) References Cited

U.S. PATENT DOCUMENTS

| 8,086,558 | B2 | 12/2011 | Dewar |
| 8,620,929 | B2 | 12/2013 | Shon et al. |
| 8,924,434 | B2 | 12/2014 | Leslie et al. |
| 2002/0183965 | A1* | 12/2002 | Gogolak ................ G16H 70/40 702/179 |
| 2012/0278336 | A1* | 11/2012 | Malik ................... G06F 40/289 707/748 |
| 2013/0138641 | A1 | 5/2013 | Korolev et al. |

(Continued)

OTHER PUBLICATIONS

Mueller et al. Abstracts from the 37th Annual Meeting of the Society of General Internal Medicine. J Gen Intern Med 29, 1-545 (2014). https://doi.org/10.1007/s11606-014-2834-9 (Year: 2014).*

(Continued)

*Primary Examiner* — Christopher L Gilligan
*Assistant Examiner* — Bennett Stephen Erickson
(74) *Attorney, Agent, or Firm* — Francis Lammes; Stephen J. Walder, Jr.; William J. Stock

(57) ABSTRACT

Mechanisms are provided that implement a drug-adverse event causality evaluation engine to identify human resource selections based on a readability of unstructured text within an individual case safety report (ICSR) and a confidence value of the ICSR. The drug-adverse event causality evaluation engine receives the ICSR from a cognitive system. The drug-adverse event causality evaluation engine analyzes the ICSR to determine a readability value of the ICSR. The drug-adverse event causality evaluation engine determines whether or not an assessment, by a human reviewer, of the ICSR is required based on a combination of the readability value of the ICSR and the confidence value. The drug-adverse event causality evaluation engine outputs an indication of whether human reviewer assessment is required.

19 Claims, 4 Drawing Sheets

(56) References Cited

U.S. PATENT DOCUMENTS

| | | | |
|---|---|---|---|
| 2013/0297347 A1* | 11/2013 | Cardoza | G06Q 50/24 705/3 |
| 2014/0067375 A1* | 3/2014 | Wooters | G06F 40/40 704/9 |
| 2016/0048655 A1* | 2/2016 | Maitra | G06F 19/3456 705/3 |
| 2018/0011977 A1* | 1/2018 | Takeda | G06K 9/6212 |
| 2019/0005019 A1* | 1/2019 | Burke | G16H 50/70 |
| 2019/0272907 A1* | 9/2019 | Aldairy | G06F 16/00 |

OTHER PUBLICATIONS

List of IBM Patent Applications Treated as Related, Nov. 1, 2018, 2 pages.

Heilman, Michael J. et al., "Combining Lexical and Grammatical Features to Improve Readability Measures for First and Second Language Texts", Association for Computational Linguistics, Proceedings of NAACL HLT 2007, Apr. 2007, 8 pages, pp. 460-467.

"Flesh-Kincaid Readability Tests", Wikipedia, https://en.wikipedia.org/wiki/Flesch%E2%80%93Kincaid_readability_tests, Downloaded from the internet on Feb. 21, 2018, 6 pages.

"Isotonic Regression", Wikipedia, https://en.wikipedia.org/wiki/Isotonic_regression, downloaded from the internet on Feb. 21, 2018, 2 pages.

Anonymously, "Confidence Score Assignment for Section-Level Evaluation and Management (E/M) Coding", IP.COM, http://ip.com/IPCOM/000243506D; Sep. 28, 2015, 5 pages.

Anonymously, "System and Method for Refined (Cognitive) Sets of Questions and Answers", IP.COM, http://ip.com/IPCOM/000247474D; Sep. 9, 2016, 5 pages.

Collins-Thompson, Kevyn, "Computational Assessment of Text Readability, A Survey of Current and Future Research"; School of Information, University of Michigan; Aug. 2014, 37 pages.

Yaneva, Victoria et al., "Evaluating the Readability of Text Simplification Output for Readers with Cognitive Disabilities", LREC 2016, Tenth International Conference on Language Resources and Evaluation, May 23-28, 2016, 7 pages.

* cited by examiner

HUMAN RESOURCE SELECTION BASED ON READABILITY OF UNSTRUCTURED TEXT WITHIN AN INDIVIDUAL CASE SAFETY REPORT (ICSR) AND CONFIDENCE OF THE ICSR

BACKGROUND

The present application relates generally to an improved data processing apparatus and method and more specifically to mechanisms for making human resource selections based on a readability of unstructured text within an individual case safety report (ICSR) and a confidence of the ICSR.

Adverse drug reactions, or ADRs, are injuries caused to a patient because of the patient taking a drug. An adverse event (AE), or adverse drug event (ADE), refers to any injury occurring at the time the patient is taking a drug, whether or not the drug itself is identified as the cause of the Thus, an ADR is a special type of AE in which a causative relationship can be shown between the drug and the adverse reaction.

ADRs may occur following a single dose of the medication (drug) or due to a prolonged administration of a drug, and may even be caused by the interaction of a combination of two or more drugs that the patient may be taking. This is different from a "side effect" in that a "side effect" may comprise beneficial effects whereas ADRs are universally negative. The study of ADRs is the concern of the field known as pharmacovigilance.

Currently, the evaluation of a case, i.e. a combination of a patient's electronic medical records from one or more electronic medical record source computing systems, for identifying adverse drug reactions, i.e. the causality of an adverse reaction with a particular drug being taken, is a highly manual process in which a human subject matter expert (SME) reviews the case and comes to a decision as to whether there is a causal relationship between a drug and an adverse reaction. However, this decision requires an evaluation of a large number of criteria and, being a manual process, is both time consuming and error prone.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions that are executed by the at least one processor to cause the at least one processor to be configured to implement a drug-adverse event causality evaluation engine to identify human resource selections based on a readability of unstructured text within an individual case safety report (ICSR) and a confidence value of the ICSR. The method comprises receiving, by the drug-adverse event causality evaluation engine, the ICSR from a cognitive system. The method further comprises analyzing, by the drug-adverse event causality evaluation engine, the ICSR to determine a readability value of the unstructured text. Additionally, the method comprises determining, by the drug-adverse event causality evaluation engine, whether or not an assessment, by a human reviewer, of the ICSR is required based on a combination of the readability value of the unstructured text and the confidence value. The method comprises outputting, by the drug-adverse event causality evaluation engine, an indication of whether human reviewer assessment is required.

Within the method, the confidence value is determined based on normalizing a probability value that indicates a level of confidence of an algorithm within the cognitive system that generated the ICSR. In determining whether or not assessment, by the human reviewer, of the ICSR is required, the method further comprises determining, by the drug-adverse event causality evaluation engine, a level of expertise of the human reviewer required to review the ICSR based on the measure of readability and the confidence value. Alternatively, in determining whether or not assessment, by the human reviewer, of the ICSR is required, the method further comprises determining, by the drug-adverse event causality evaluation engine, a number of human reviewers required to review the ICSR based on the measure of readability and the confidence value.

In determining whether or not assessment, by the human reviewer, of the ICSR is required, the method further comprises calculating, by the drug-adverse event causality evaluation engine, a sum of a weighted measure of readability and a weighted confidence value. In determining whether or not assessment, by the human reviewer, of the ICSR is required, the method further comprises utilizing, by the drug-adverse event causality evaluation engine, a first threshold to determine whether assessment, by the human reviewer, of the ICSR is required; and utilizing, by the drug-adverse event causality evaluation engine, one or more other thresholds to determine a level of expertise of the human reviewer required to review the ICSR in response to assessment by the human reviewer of the ICSR being required. Within the method, the cognitive system is a pharmacovigilance cognitive medical system.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
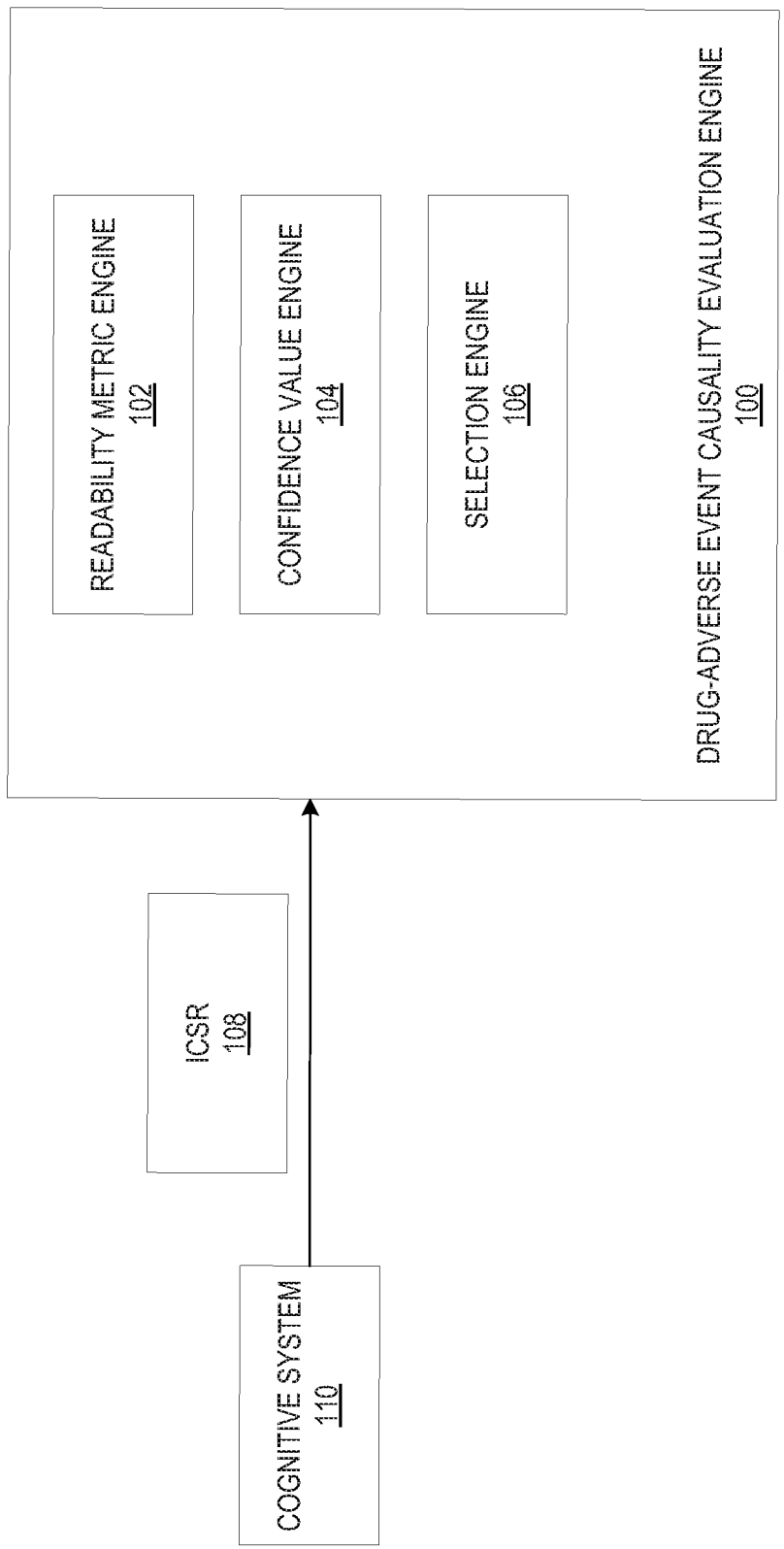
FIG. 1 is an example block diagram illustrating components of a drug-adverse event causality evaluation engine in accordance with one illustrative embodiment.

Causality assessment is vital to pharmacovigilance processes in the pharmaceutical industry and plays a role in important decisions, such as whether to make a change in a drug label. Moreover, causality assessment is important in other aspects of the practice of medicine, such as making decisions as to a patient's treatment, diagnosing the cause of adverse events (AE) (or adverse drug reaction (ADR)) with regard to drugs that are taken, and the like. Currently, an individual case safety report (ICSR) associated with a causality identifies a drug and an adverse event (AE) pair using chemical structure properties, drug-drug interaction properties, and protein structure properties, as well as several patient and disease characteristics, e.g., patient identifier, reporter identifier, drug-food interaction, drug-disease interaction, temporal cues, dechallenge/rechallenge characteristics, etc., which may be provided in the patient's electronic medical records (EMRs). These are collectively referred to as "causality factors" herein. The ICSR may also include causality prediction scores that are calculated with regard to these various causality factors based on a plurality of causality models, each causality model being specifically configured and trained to evaluate specific ones of the causality factors and generate a corresponding causality prediction score for that causality factor.

The causality prediction score is indicative of the likelihood that the AE is caused by the taking of the drug in the drug-AE pairing. The single integrated causality prediction score may be evaluated against one or more threshold values indicating a minimum causality prediction score required to identify a valid causality link between a drug and AE in the drug-AE pair. If the integrated causality prediction score meets or exceeds the threshold value, then it may be regarded as an actual valid causality link indicating that, the drug is a cause of the AE (or ADR) for this patient. If the integrated causality prediction score does not meet the threshold value, then the drug-AE pair does not represent a valid causality link of the drug with the AE for this patient. A corresponding notification or output of the results of such a comparison may be generated indicating whether or not a valid causality link exists between the drug and the AE (or ADR).

This evaluation of drug-AE pairs may be done for each possible drug-AE pair being considered, e.g., a listing of drugs to be considered and a particular AE, or a particular drug to be considered and a listing of particular AEs to be considered. Thus, in one sense, a user may wish to know all the possible AEs (or ADRs) that have a relatively high likelihood of being caused by the taking of a particular drug with patients of various characteristics, or with regard to a particular patient, i.e. a particular set of patient characteristics. In another sense, a user may wish to know, for a given AE, what drugs the patient is taking that may have caused the AE. In some cases, the drug-AE pairings may be evaluated with regard to multiple drugs and multiple AEs so as to determine particular combinations of drugs that the patient may be taking that each may be contributing to particular AEs (or ADRs) the patient is experiencing or is likely to experience.

Currently, the generated ICSR is assessed qualitatively by a human reviewer, hereinafter referred to as a subject matter expert (SME), based on their own individual expertise, with little or no interaction of the contributors with one another. As a result, there is low inter-contributor agreement, i.e. two different subject matter experts may disagree as to the qualitative assessment of causality between a drug and an adverse event (AE) (or ADR). Moreover, because of the manual qualitative evaluation based on individual human SME experience and expertise, there is a large variation in the assessments, some of which may be erroneous due to human error or a lack of consideration of all possible factors since causality is a very complex evaluation which may require evaluation of a large number of different factors. For example, the Council for International Organizations of Medical Sciences (CIOMS) has specified the following criteria for evaluating drug safety:

1. Criteria to consider when reviewing a signal, i.e. an indicator of an adverse drug reaction (ADR) from a case series (e.g., a set of patient electronic medical record (EMR) data for a patient) or other sources:
   Rechallenge/Dechallenge (a medical testing protocol in which a medicine or drug is administered, withdrawn, then re-administered, while being monitored for adverse effects at each stage); known mechanism, e.g., class effect (a drug effect produced by all members of a chemically related group of drugs and not only by a single drug from that class); biological plausibility (i.e. the proposal of a causal relationship); consistent time-to-onset (temporality); observed in drug-drug, drug-disease, drug-food interaction, etc.
2. Clinical data: Pharmacodynamic, pharmacokinetic, and/or interaction studies; consistent outcome in study investigating drug-AE association; etc.
3. Preclinical data in well-designed studies: Similar findings in animals; positive in vitro or ex vivo tests.
4. Product quality data.

Each of these categories of criteria may comprise a large number of individual parameters and characteristics, and combinations of parameters and characteristics, which may influence the evaluation of the criteria.

Accordingly, because an ICSR may be very complex, some ICSRs should be assessed by a seasoned SME while other ICSRs may be assessed by an early-professional SME. Further, some ICSRs may not need SME assessment, where other ICSRs may require assessment by an SME. Thus, the illustrative embodiment provides a drug-adverse event causality evaluation engine which leverages the computing power of specifically configured computing systems as well as cognitive logic that emulates the thinking processes of human beings, to specifically identify both a readability of an ICSR and confidence for evaluating the ICSR based on an analysis of natural language text within the ICSR. The drug-adverse event causality evaluation engine then utilizes the readability and confidence to determine whether a SME is required for assessment of the ICSR and, if so, what expertise level is needed for assessment of the ICSR. If an SME assessment is required and with the level of expertise of the required SME determined, the identified SME may assess causal relationships between the drug and the adverse events or adverse drug reactions (ADRs), taking into account the large number of criteria and complex relationships between various properties of the drug and adverse reactions, so as to identify adverse drug reactions (ADRs) that have a causal link to the taking of the drug by patients. The ADRs may then be used to inform pharmaceutical providers that may provide the drug, so that they may make modifications to guides, drug labels, or other documentation associated with the drug based on the identified causal links between the drug and ADRs, or even make modifications to the drug itself. In some illustrative embodiments, the output of the causal relationships may be used to inform medical personnel of the ADRs so that appropriate treatment of the patient may be performed. Moreover, in some illustrative embodiments, the identified ADRs may be input to other cognitive logic for performance of cognitive operations to support decision making, such as in a decision support system.

Because the mechanisms of the illustrative embodiments provide automated specialized computing systems for identifying whether an SME is required for assessment of the ICSR and a level of expertise of the SME if required, the mechanisms of the illustrative embodiments may evaluate a relatively large and complex set of causality factors that is not feasible for the previous manual evaluations. Moreover, the automated specialized computing systems further allow for such evaluations that do not suffer from the drawbacks of human error, which is likely in the previous manual assignments of an SME to review ICSRs. Such assignments may be performed much more quickly and provide more accurate results with regard to a relatively larger number of possible drug-AE pairs. All of these improvements serve to improve the decision making of medical personnel by providing decision support services that provide additional information upon which the medical personnel may base their treatment decisions for a particular patient. Moreover, in some illustrative embodiments, the improvements improve the operation of a cognitive system when performing decision support services such as diagnostic services, treatment recommendation services, or the like.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general-purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine-readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for automatically determining whether a subject matter expert (SME) is required for assessment and, if so, an expertise level of the SME to assess an individual case safety report (ICSR) associated with a drug-adverse event. FIG. 1 is an example block diagram illustrating components of a drug-adverse event causality evaluation engine in accordance with one illustrative embodiment. As shown in FIG. 1, drug-adverse event causality evaluation engine 100 comprises readability metric engine 102, confidence value engine 104, and selection engine 106. Responsive to drug-adverse event causality evaluation engine 100 receiving ICSR 108 from cognitive system 110, readability metric engine 102 examines a readability level of unstructured natural language text within ICSR 108 in terms of the language and writing style. That is, readability metric engine 102 analyzes the unstructured natural language text within ICSR 108 looking for components such as word length, sentence length, average number of words per sentence, number of syllables for each word, average number of syllables per word, or the like. Utilizing the identified components, readability metric engine 102 computes readability value (R) for ICSR 108 using, for example but not limited to, a Flesch-Kincaid readability test, a Coleman-Liau index, a Gunning Fog index, or the like.

Confidence value engine 104 then identifies a probability value associated with ICSR 108, i.e. whether ICSR 108 is a valid ICSR. A valid ICSR should comprise an identifiable patient, an identifiable reporter, an adverse event, and a drug. That is, when cognitive system 110. Which may be a pharmacovigilance cognitive medical system, produces an ICSR, such as ICSR 108, cognitive system 110 generates a probability value that indicates a level of confidence of an algorithm within cognitive system 110 that generated ICSR 108, i.e. whether the ICSR is valid or invalid based on the ICSR having the required elements of a valid ICSR. However, the raw probability values generated by such algorithms within cognitive systems, such as cognitive system 110, may be misleading, especially the probability values generated by neural network architecture cognitive systems. Hence, confidence value engine 104 normalizes the probability values of the output using a regression, such as but not limited to an isotonic regression, monotonic regression, or the like, using a validation dataset to generate a confidence value (C). Confidence value engine 104 utilizes the normalization process to make sure that when cognitive system 110 generates a probability value as x %, it means x out of 100 outputs which has a true confidence value x. For example, if the output has 80% confidence, then in 100 instances with 80% confidence, 80 of the outputs are guaranteed to be correct.

With the readability value (R) and normalized confidence value (C) identified, selection engine 106 determines a human intervention value (Y) using a sum of a weighted readability value (R) and a weighted confidence value (C). Specifically, selection engine 106 utilizes weights a and b, where a+b=1, to determine human intervention value (Y), such that:

$$Y=aR+bC.$$

The values of weights a and b may be learned through regression techniques on a validation dataset. That is, based on how well drug-adverse event causality evaluation engine 100 analyzes ICSRs and identifies the need for SME assessment and an expertise level of the SME assigned to assess the ICSRs if required, the feedback of the selection(s) may be utilized to train drug-adverse event causality evaluation engine 100 and adjust the values of weights a and b while adhering to the constraint of where a+b=1.

Once selection engine 106 has determined the human intervention value (Y) for ICSR 108, selection engine 106 utilizes one or more thresholds to determine whether an SME is required to assess ICSR 108 and, if so, an expertise level of the SME. For example, utilizing a first threshold $t_1$, if selection engine 106 determines that human intervention value (Y) is greater than the first threshold $t_1$, then selection engine 106 may determine that no human assessment of ICSR 108 is required. However, if selection engine 106 determines that human intervention value (Y) is less than or equal to the first threshold $t_1$ but greater than a second threshold $t_2$, then selection engine 106 may determine that an early-professional SME should assess ICSR 108. Finally, if selection engine 106 determines that human intervention value (Y) is less than or equal to the second threshold $t_2$, then selection engine 106 may determine that a seasoned SME should assess ICSR 108. As with the weights a and b above, feedback of the selection(s) may be utilized to train drug-adverse event causality evaluation engine 100 and adjust first threshold $t_1$ and second threshold $t_2$.

It should be noted that the above example only utilizes two levels of expertise, i.e. an early-professional SME and a seasoned SME. If more than two levels of expertise are available in determined which SME to utilize, then the illustrative embodiments recognize that additional thresholds would be used to classify each level of expertise required. It should also be noted that while the above examples only illustrate assigning one SME if an assessment is deemed required, more than one SME may be assigned to any given assessment. For example, if a third threshold $t_3$ is used and if selection engine 106 determines that human intervention value (Y) is less than second threshold $t_2$ but greater than third threshold $t_3$, then selection engine 106 may determine that an seasoned SME should assess ICSR 108. However, if selection engine 106 determines that human intervention value (Y) is less than third threshold $t_3$, then selection engine 106 may determine that not only should a seasoned SME assess ICSR 108 but two or more seasoned SMEs are required.

Both the weights, such as weights a and b, and the thresholds, such as thresholds $t_1$, $t_2$, $t_3$, etc., may initially be estimated by based on available training data, which will improve the accuracy and quality of the determination of whether an assessment should be performed as well as, if an assessment is to be performed, what level of expertise is required. It must be noted that given enough training data the impact of readability may be minimize as the algorithm sees enough difficult examples. This can be controlled with weight a in the in determining the human intervention value (Y).

Thus, drug-adverse event causality evaluation engine leverages the computing power of specifically configured computing systems as well as cognitive logic that emulates the thinking processes of human beings, to specifically identify both a readability of an ICSR and confidence for evaluating the ICSR based on an analysis of natural language text within the ICSR. The drug-adverse event causality evaluation engine then utilizes the readability and confidence to determine Whether a SME is required for assessment of the ICSR and, if so, what expertise level is needed for assessment of the ICSR.

Figure 2:
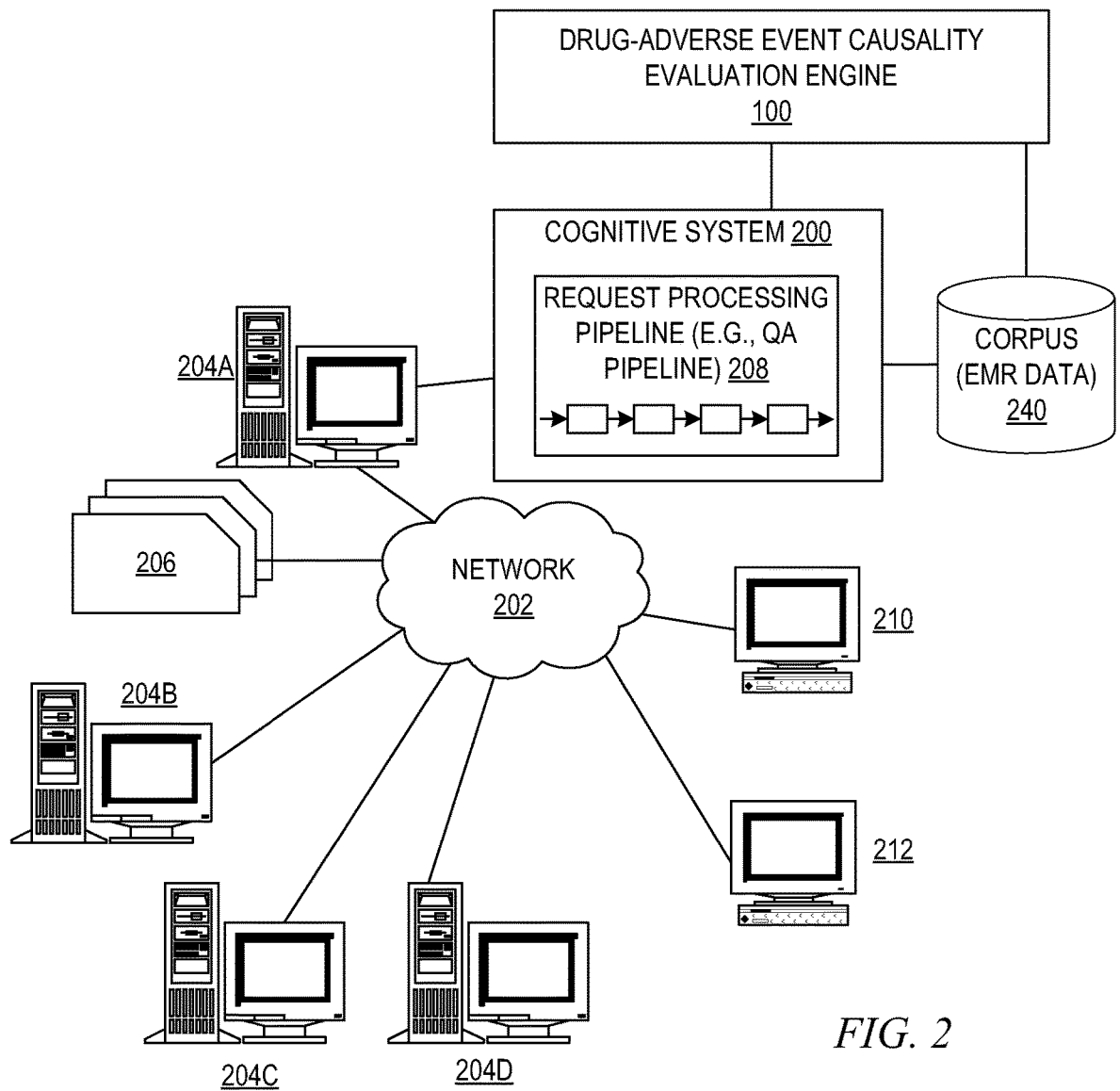
FIG. 2 depicts a schematic diagram of one illustrative embodiment of a cognitive healthcare system in a computer network.
Figure 3:
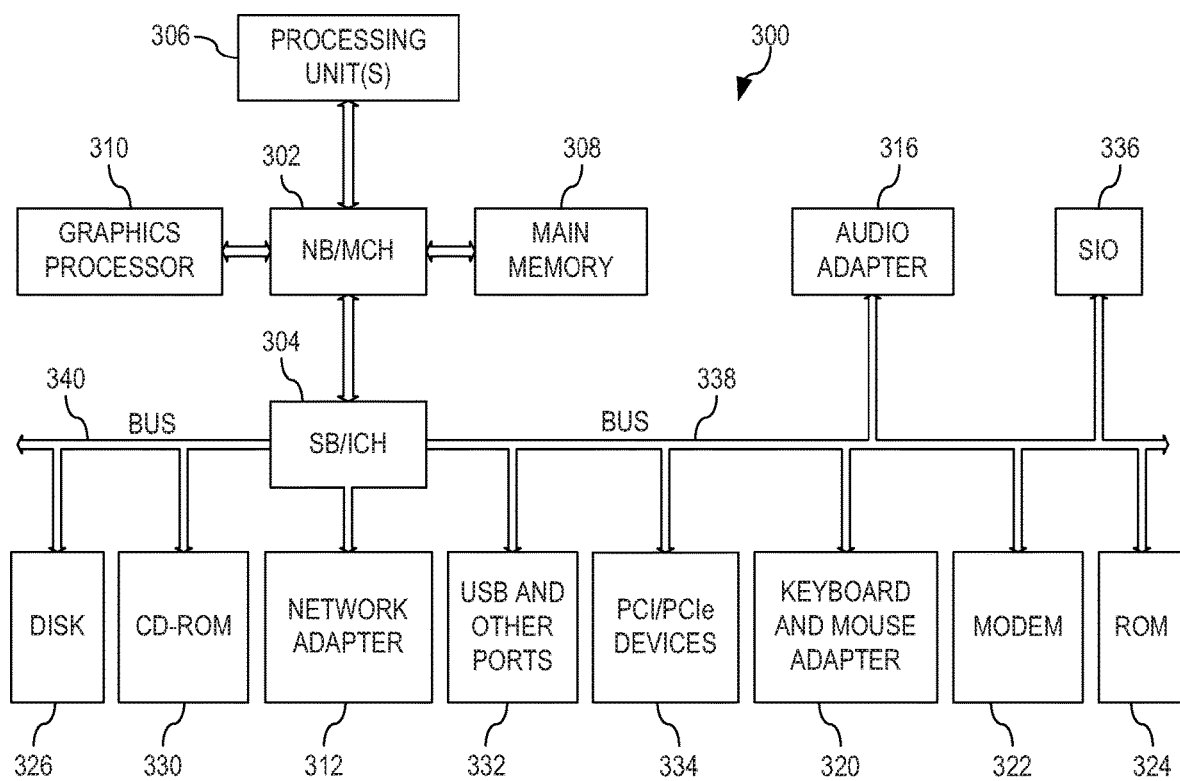
FIG. 3 is a block diagram of an example data processing system in which aspects of the illustrative embodiments are implemented.

It is clear from the above, that the illustrative embodiments may be utilized in many different types of data processing environments. In order to provide a context for the description of the specific elements and functionality of the illustrative embodiments, FIGS. 2-3 are provided hereafter as example environments in which aspects of the illustrative embodiments may be implemented. It should be appreciated that FIGS. 2-3 are only examples and are not intended to assert or imply any limitation with regard to the environments in which aspects or embodiments of the present invention may be implemented. Many modifications to the depicted environments may be made without departing from the spirit and scope of the present invention.

It should be noted that the mechanisms of the illustrative embodiments need not be utilized with a cognitive system. To the contrary, the illustrative embodiments may be implemented as a standalone DAP causality evaluation engine implemented on one or more computing devices or systems. The standalone DAP causality evaluation engine may generate an output notification that may be utilized by a user when evaluating a particular drug, adverse event, or the combination of drug and adverse event. Thus, in a standalone implementation, the drug-adverse event causality evaluation engine may be implemented using one or more computing devices or systems such as depicted in FIG. 3, as one example. However, to illustrate further functionality of illustrative embodiments of the present invention FIGS. 2-3 are provided to illustrate the way in which the drug-adverse event causality evaluation engine may be utilized with a cognitive system to perform cognitive healthcare operations for diagnosing or treating a patient.

FIGS. 2-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for identifying whether an SME is required for assessment of the ICSR and a level of expertise of the SME if required based on an analysis of natural language text within the ICSR analyzed by the drug-adverse event causality evaluation engine of the illustrative embodiments.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

The request processing pipelines may utilize the analysis performed by the drug-adverse event causality evaluation engine of one or more of the illustrative embodiments, such as drug-adverse event causality evaluation engine 100 in FIG. 1, as a factor considered by the request processing pipeline when performing cognitive evaluations of a patient to determine a diagnosis of the patient, determine a recommended treatment for the patient, and/or monitor the patient, with an aim at minimizing adverse drug reactions for drugs taken by the patient.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments for identifying whether an SME is required for assessment of the ICSR and a level of expertise of the SME if required based on an analysis of natural language text within the ICSR analyzed by the drug-adverse event causality evaluation engine of the illustrative embodiments. It should be appreciated that while embodiments of the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 2-3 are only examples and are not intended to state or imply any limitation with regard to the type of cognitive system mechanisms with which the illustrative embodiments are implemented. Many modifications to the example cognitive system shown in FIGS. 2-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding,
Ingest and process vast amounts of structured and unstructured data,
Generate and evaluate hypothesis,
Weigh and evaluate responses that are based only on relevant evidence,
Provide situation-specific advice, insights, and guidance,
Improve knowledge and learn with each iteration and interaction through machine learning processes,
Enable decision making at the point of impact (contextual guidance),
Scale in proportion to the task,
Extend and magnify human expertise and cognition,
Identify resonating, human-like attributes and traits from natural language,
Deduce various language specific or agnostic attributes from natural language,
High degree of relevant recollection from data points (images, text, voice) (memorization and recall),
Predict and sense with situational awareness that mimic human cognition based on experiences, or
Answer questions based on natural language and specific evidence.

In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these questions and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest-ranking score or confidence measure, or which is a best match to the input question, or a combination of ranked listing and final answer.

With regard to the drug-adverse event causality evaluation engine of the illustrative embodiments, the recommendations generated by the drug-adverse event causality evaluation engine may be input to the QA pipeline for use as yet another portion of the corpus or corpora upon which the QA pipeline operates. For example, the recommendations generated by the drug-adverse event causality evaluation engine may be included in inputs upon which the operations of the reasoning algorithms are applied, as part of the evaluation of evidence supporting various candidate answers or responses generated by the QA pipeline, or the like. Thus, the reasoning algorithms may include factors for identifying whether an SME is required for assessment of the ICSR and a level of expertise of the SME if required based on an analysis of natural language text within the ICSR.

FIG. 2 depicts a schematic diagram of one illustrative embodiment of a cognitive system 200 implementing a request processing pipeline 208, which in some embodiments may be a question answering (QA) pipeline, in a computer network 202. For purposes of the present description, it will be assumed that the request processing pipeline 208 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 200 is implemented on one or more computing devices 204A-D (comprising one or more processors and one or more memories, and potentially any other computing device elements generally known in the art including buses, storage devices, communication interfaces, and the like) connected to the computer network 202. For purposes of illustration only, FIG. 2 depicts the cognitive system 200 being implemented on computing device 204A only, but as noted above the cognitive system 200 may be distributed across multiple computing devices, such as a plurality of computing devices 204A-D. The network 202 includes multiple computing devices 204A-D, which may operate as server computing devices, and 210-212 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 200 and network 202 enables question processing and answer generation (QA) functionality for one or more cognitive system users via their respective computing devices 210-212. In other embodiments, the cognitive system 200 and network 202 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 200 may be used with components, systems, subsystems, and/or devices other than those that are depicted herein.

The cognitive system 200 is configured to implement a request processing pipeline 208 that receive inputs from various sources. The requests may be posed in the form of a natural language question, natural language request for information, natural language request for the performance of a cognitive operation, or the like. For example, the cognitive system 200 receives input from the network 202, a corpus or corpora of electronic documents 206, cognitive system users, and/or other data and other possible sources of input. In one embodiment, some or all of the inputs to the cognitive system 200 are routed through the network 202. The various computing devices 204A-D on the network 202 include access points for content creators and cognitive system users. Some of the computing devices 204A-D include devices for a database storing the corpus or corpora of data 206 (which is shown as a separate entity in FIG. 2 for illustrative purposes only). Portions of the corpus or corpora of data 206 may also be provided on one or more other network attached storage devices, in one or more databases, or other computing devices not explicitly shown in FIG. 2. The network 202 includes local network connections and remote connections in various embodiments, such that the cognitive system 200 may operate in environments of any size, including local and global, e.g., the Internet.

In one embodiment, the content creator creates content in a document of the corpus or corpora of data 206 for use as part of a corpus of data with the cognitive system 200. The document includes any file, text, article, or source of data for use in the cognitive system 200. Cognitive system users access the cognitive system 200 via a network connection or an Internet connection to the network 202, and input questions/requests to the cognitive system 200 that are answered/processed based on the content in the corpus or corpora of data 206. In one embodiment, the questions/requests are formed using natural language. The cognitive system 200 parses and interprets the question/request via a pipeline 208, and provides a response to the cognitive system user, e.g., cognitive system user 210, containing one or more answers to the question posed, response to the request, results of processing the request, or the like. In some embodiments, the cognitive system 200 provides a response to users in a ranked list of candidate answers/responses while in other illustrative embodiments, the cognitive system 200 provides a single final answer/response or a combination of a final answer/response and ranked listing of other candidate answers/responses.

The cognitive system 200 implements the pipeline 208 which comprises a plurality of stages for processing an input question/request based on information obtained from the corpus or corpora of data 206. The pipeline 208 generates answers/responses for the input question or request based on the processing of the input question/request and the corpus or corpora of data 206.

In some illustrative embodiments, the cognitive system 200 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 206. Based on the application of the queries to the corpus or corpora of data 206, a set of hypotheses, or candidate answers/responses to the input question/request, are generated by looking across the corpus or corpora of data 206 for portions of the corpus or corpora of data 206 (hereafter referred to simply as the corpus 206) that have some potential for containing a valuable response to the input question/response (hereafter assumed to be an input question). The pipeline 208 of the IBM Watson™ cognitive system then performs deep analysis on the language of the input question and the language used in each of the portions of the corpus 206 found during the application of the queries using a variety of reasoning algorithms.

The scores obtained from the various reasoning algorithms are then weighted against a statistical model that summarizes a level of confidence that the pipeline 208 of the IBM Watson™ cognitive system 200, in this example, has regarding the evidence that the potential candidate answer is inferred by the question. This process is repeated for each of the candidate answers to generate a ranked listing of candidate answers which may then be presented to the user that submitted the input question, e.g., a user of client computing device 210, or from which a final answer is selected and presented to the user. More information about the pipeline 208 of the IBM Watson™ cognitive system 200 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 200 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result. In particular, the mechanisms of the healthcare based cognitive system may process drug-adverse events or adverse drug reaction pairings when performing the healthcare oriented cognitive system result, e.g., a diagnosis or treatment recommendation.

In the context of the present invention, cognitive system 200 may' provide a cognitive functionality for assisting with healthcare based operations. For example, depending upon the particular implementation, the healthcare based operations may comprise patient diagnostics, medical treatment recommendation systems, personal patient, care plan generation and monitoring, patient electronic medical record (EMR) evaluation for various purposes, such as for identifying patients that are suitable for a medical trial or a particular type of medical treatment, or the like. Thus, the cognitive system 200 may be a healthcare cognitive system 200 that operates in the medical or healthcare type domains and which may process requests for such healthcare operations via the request processing pipeline 208 input as either structured or unstructured requests, natural language input questions, or the like. In one illustrative embodiment, the cognitive system 200 is a medical treatment recommendation system that analyzes a patient's electronic medical records (EMRs) in relation to medical guidelines and other medical documentation in a corpus of information 240, and further analyze natural language text within the ICSR in order to identify whether an SME is required for assessment of the ICSR and a level of expertise of the SME if required.

As shown in FIG. 2, the cognitive system 200 is further augmented, in accordance with the mechanisms of the illustrative embodiments, to include logic implemented in specialized hardware, software executed on hardware, or any combination of specialized hardware and software executed on hardware, for implementing drug-adverse event causality evaluation engine 100. As described previously, the drug-adverse event causality evaluation engine 100 identifies both a readability of an ICSR and confidence for evaluating the ICSR based on an analysis of natural language text within the ICSR. The drug-adverse event causality evaluation engine then utilizes the readability and confidence to determine whether a SME is required for assessment of the report and, if so, what expertise level is needed for assessment of the report.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 3 is provided as an example of one type of data processing system in which aspects of the present invention may be implemented. Many other types of data processing systems may be likewise configured to specifically implement the mechanisms of the illustrative embodiments.

FIG. 3 is a block diagram of an example data processing system in which aspects of the illustrative embodiments are implemented. Data processing system 300 is an example of a computer, such as server 204A or client 210 in FIG. 2, in which computer usable code or instructions implementing the processes for illustrative embodiments of the present invention are located. In one illustrative embodiment, FIG. 3 represents a server computing device, such as a server 204, which, which implements a cognitive system 200 and QA system pipeline 208 augmented to include the additional mechanisms of the illustrative embodiments described hereafter.

In the depicted example, data processing system 300 employs a hub architecture including North Bridge and Memory Controller Hub (NB/MCH) 302 and South Bridge and Input/Output (I/O) Controller Hub (SB/ICH) 304. Processing unit 306, main memory 308, and graphics processor 310 are connected to NB/MCH 302. Graphics processor 310 is connected to NB/MCH 302 through an accelerated graphics port (AGP).

In the depicted example, local area network (LAN) adapter 312 connects to SB/ICH 304. Audio adapter 316, keyboard and mouse adapter 320, modem 322, read only memory (ROM) 324, hard disk drive (HDD) 326, CD-ROM drive 330, universal serial bus (USB) ports and other communication ports 332, and PCI/PCIe devices 334 connect to SB/ICH 304 through bus 338 and bus 340. PCI/PCIe devices may include, for example, Ethernet adapters, add-in cards, and PC cards for notebook computers. PCI uses a card bus controller, while PCIe does not. ROM 324 may be, for example, a flash basic input/output system (BIOS).

HDD 326 and CD-ROM drive 330 connect to SB/ICH 304 through bus 340, HDD 326 and CD-ROM drive 330 may use, for example, an integrated drive electronics (IDE) or serial advanced technology attachment (SATA) interface. Super I/O (SK)) device 336 is connected to SB/ICH 304.

An operating system runs on processing unit 306. The operating system coordinates and provides control of various components within the data processing system 300 in FIG. 3. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 300.

As a server, data processing system 300 may be, for example, an IBM™ eServer™ System p® computer system, running the Advanced Interactive Executive (AIX®) operating system or the LINUX® operating system. Data processing system 300 may be a symmetric multiprocessor (SMP) system including a plurality of processors in processing unit 306. Alternatively, a single processor system may be employed.

Instructions for the operating system, the object-oriented programming system, and applications or programs are located on storage devices, such as HDD 326, and are loaded into main memory 308 for execution by processing unit 306. The processes for illustrative embodiments of the present invention are performed by processing unit 306 using computer usable program code, which is located in a memory such as, for example, main memory 308, ROM 324, or in one or more peripheral devices 326 and 330, for example.

A bus system, such as bus 338 or bus 340 as shown in FIG. 3, is comprised of one or more buses. Of course, the bus system may be implemented using any type of communication fabric or architecture that provides for a transfer of data between different components or devices attached to the fabric or architecture. A communication unit, such as modem 322 or network adapter 312 of FIG. 3, includes one or more devices used to transmit and receive data. A memory may be, for example, main memory 308, ROM 324, or a cache such as found in NB/MCH 302 in FIG. 3.

Those of ordinary skill in the art will appreciate that the hardware depicted in FIGS. 2 and 3 may vary depending on the implementation. Other internal hardware or peripheral devices, such as flash memory, equivalent non-volatile memory, or optical disk drives and the like, may be used in addition to or in place of the hardware depicted in FIGS. 2 and 3. Also, the processes of the illustrative embodiments may be applied to a multiprocessor data processing system, other than the SMP system mentioned previously, without departing from the spirit and scope of the present invention.

Moreover, the data processing system 300 may take the form of any of a number of different data processing systems including client computing devices, server computing devices, a tablet computer, laptop computer, telephone or other communication device, a personal digital assistant (PDA), or the like. In some illustrative examples, data processing system 300 may be a portable computing device that is configured with flash memory to provide non-volatile memory for storing operating system files and/or user-generated data, for example. Essentially, data processing system 300 may be any known or later developed data processing system without architectural limitation.

Figure 4:
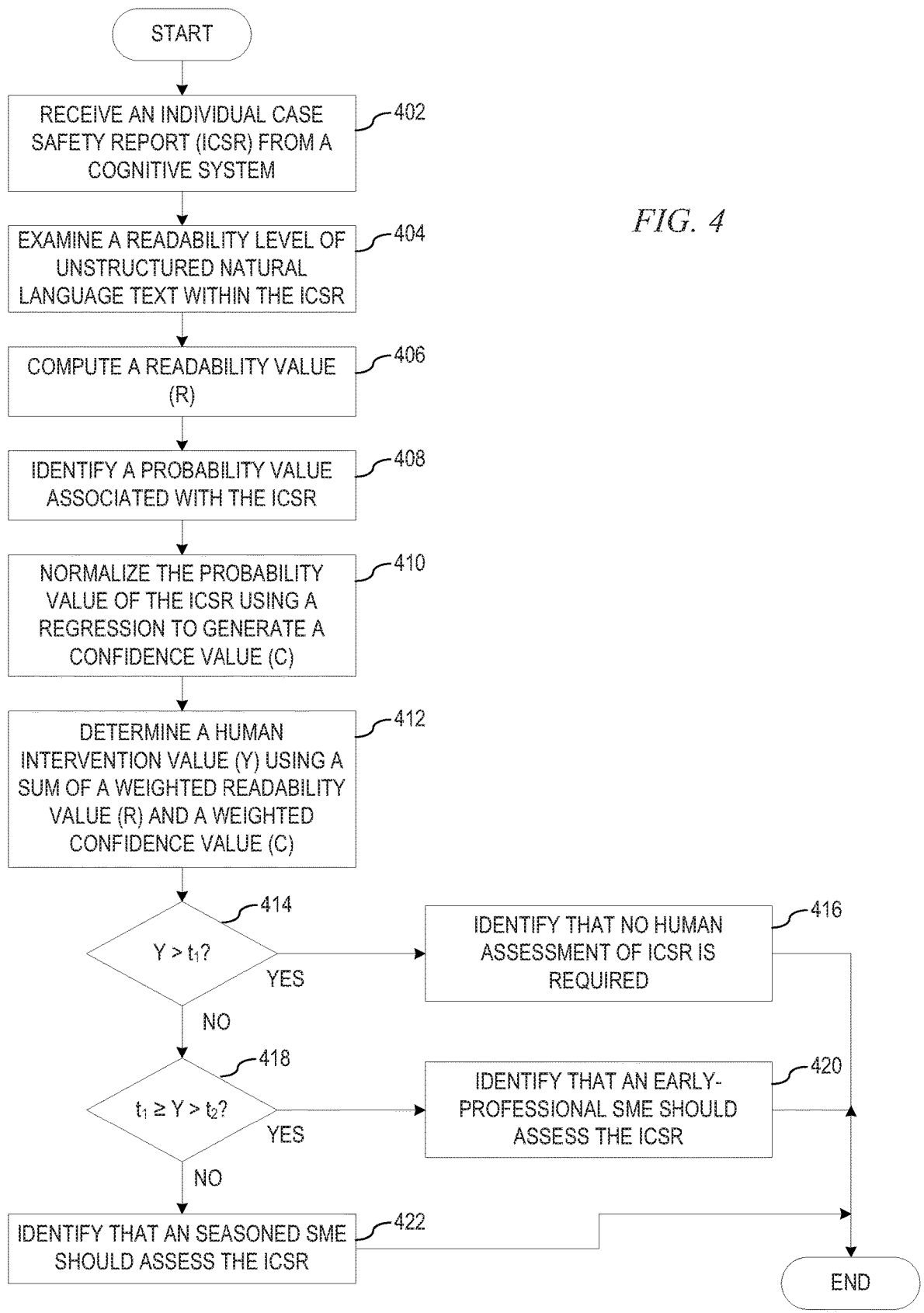
FIG. 4 is a flowchart outlining an example operation of a drug-adverse event causality evaluation engine in accordance with one illustrative embodiment.

FIG. 4 is a flowchart outlining an example operation of a drug-adverse event causality evaluation engine in accordance with one illustrative embodiment. As the exemplary operation begins, the drug-adverse event causality evaluation engine receives an individual case safety report (ICSR) from a cognitive system, which may be a pharmacovigilance cognitive medical system (step 402). A readability metric engine within the drug-adverse event causality evaluation engine examines a readability level of unstructured natural language text within the ICSR in terms of the language and writing style (step 404). That is, the readability metric engine analyzes the unstructured natural language text within the ICSR looking for components such as word length, sentence length, average number of words per sentence, number of syllables for each word, average number of syllables per word, or the like. Utilizing the identified components, the readability metric engine computes a readability value (R) for the ICSR (step 406). To computer the readability value, the readability engine may use, for example but not limited to, a Flesch-Kincaid readability test, a Coleman-Liau index, a Gunning Fog index, or the like.

A confidence value engine within the drug-adverse event causality evaluation engine then identifies a probability value associated with the ICSR, i.e. whether ICSR 108 is a valid ICSR (step 408). A valid ICSR should comprise an identifiable patient, an identifiable reporter, an adverse event, and a drug. That is, when the cognitive system produces the ICSR, the cognitive system also generates a probability value that indicates a level of confidence of an algorithm within the cognitive system that generated the ICSR, i.e. whether the ICSR is valid or invalid based on the ICSR having the required elements of a valid ICSR. However, the raw probability values generated by such algorithms within cognitive systems may be misleading, especially the probability values generated by neural network architecture cognitive systems. Thus, confidence value engine normalizes the probability value of the ICSR using a regression to generate a confidence value (C) (step 410). To normalize the probability value and generate the confidence value (C), the confidence value engine may use, for example but not limited to, an isotonic regression, monotonic regression, or the like, using a validation dataset. The confidence value engine utilizes the normalization process to make sure that when the cognitive system generates a probability value as x %, it means x out of 100 outputs which has a true confidence value x. For example, if the output has 80% confidence, then in 100 instances with 80% confidence, 80 of the outputs are guaranteed to be correct.

With the readability value (R) and normalized confidence value (C) identified, a selection engine within the drug-adverse event causality evaluation engine determines a human intervention value (Y) using a sum of a weighted readability value (R) and a weighted confidence value (C) (step 412). Specifically, the selection engine utilizes weights a and b, where a+b=1, to determine human intervention value (Y), such that:

$$Y=aR+bC.$$

The values of weights a and b may be learned through regression techniques on a validation dataset. That is, based on how well the drug-adverse event causality evaluation engine analyzes ICSRs and identifies the need for SME assessment and an expertise level of the SME assigned to assess the ICSRs if required, the feedback of the selection(s) may be utilized to train the drug-adverse event causality evaluation engine and adjust the values of weights a and h while adhering to the constraint of where a+b=1.

Once the selection engine has determined the human intervention value (Y) for the ICSR, the selection engine utilizes one or more thresholds to determine whether an SME is required to assess ICSR and, if so, an expertise level of the SME. In this exemplary embodiment, the selection engine determines whether the human intervention value (Y) is greater than first threshold $t_1$ (step 414). If at step 414 the selection engine determines that the human intervention value (Y) is greater than first threshold $t_1$, the selection engine identifies that no human assessment of ICSR is required (step 416). However, if at step 414 the selection engine determines that the human intervention value (Y) is less than or equal to the first threshold $t_1$, then the selection engine determines whether the human intervention value (Y) is less than or equal to the first threshold $t_1$ but greater than a second threshold $t_2$ (step 418), if at step 418 the selection engine determines that the human intervention value (Y) is less than or equal to the first threshold $t_1$ but greater than the second threshold $t_2$, then the selection engine identifies that an early-professional SME should assess the ICSR (step 420). If at step 418 the selection engine determines that the human intervention value (Y) is less than or equal to the second threshold $t_2$, then the selection engine identifies that a seasoned SME should assess the ICSR (step 422). Feedback of the selection(s) may be utilized to train drug-adverse event causality evaluation engine and adjust first threshold $t_1$ and second threshold $t_2$.

It should be noted that the above example only utilizes two levels of expertise, i.e. an early-professional SME and a seasoned SME. If more than two levels of expertise are available in determined which SME to utilize, then the illustrative embodiments recognize that additional thresholds would be used to classify each level of expertise required. It should also be noted that while the above examples only illustrate assigning one SME if an assessment is deemed required, more than one SME may be assigned to any given assessment. For example, if a third threshold $t_3$ is used and if the selection engine determines that human intervention value (Y) is less than second threshold $t_2$ but greater than third threshold $t_3$, then the selection engine may determine that an seasoned SME should assess the ICSR. However, if the selection engine determines that human intervention value (Y) is less than third threshold $t_3$, then the selection engine 106 may determine that not only should a seasoned SME assess the ICSR but two or more seasoned SMEs are required to assess the ICSR.

Both the weights, such as weights a and b, and the thresholds, such as thresholds $t_1$, $t_2$, $t_3$, etc., may initially be estimated by based on available training data, which will improve the accuracy and quality of the determination of whether an assessment should be performed as well as, if an assessment is to be performed, what level of expertise is required. It must be noted that given enough training data the impact of readability may be minimize as the algorithm sees enough difficult examples. This can be controlled with weight a in the in determining the human intervention value (Y). From steps 416, 420, and 422, the operation terminates.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions that are executed by the at least one processor to cause the at least one processor to be configured to implement a drug-adverse event causality evaluation engine to identify human resource selections based on a readability of unstructured natural language text within an individual case safety report (ICSR) and a confidence value of the ICSR, the method comprising:

receiving, by the drug-adverse event causality evaluation engine, the ICSR from a cognitive system;

analyzing, by the drug-adverse event causality evaluation engine, the unstructured natural language text within the ICSR to determine a readability value of the ICSR;

normalizing, by the drug-adverse event causality evaluation engine, a probability value indicating a level of confidence of an algorithm within the cognitive system that generated the ICSR thereby generating the confidence value of the ICSR;

determining, by the drug-adverse event causality evaluation engine, whether or not an assessment, by a human reviewer, of the ICSR is required based on a combination of the readability value of the ICSR and the confidence value of the ICSR by using regression techniques to learn a set of weights that are used to weight the readability value of the ICSR and the confidence value of the ICSR, wherein the set of weights for the readability value of the ICSR and the confidence value of the ICSR meet a defined constraint and wherein the set of weights are adjusted based on a training of the drug-adverse event causality engine so as to adhere to the defined constraint; and processing, by the drug-adverse event causality evaluation engine, the ICSR based on the determination of whether the human reviewer assessment is required.

2. The method of claim 1, wherein determining whether or not the assessment, by the human reviewer, of the ICSR is required further comprises:

determining, by the drug-adverse event causality evaluation engine, a level of expertise of the human reviewer required to review the ICSR based on the readability value and the confidence value of the ICSR.

3. The method of claim 1, wherein determining whether or not the assessment, by the human reviewer, of the ICSR is required further comprises:

determining, by the drug-adverse event causality evaluation engine, a number of human reviewers required to review the ICSR based on the readability value and the confidence value of the ICSR.

4. The method of claim 1, wherein determining whether or not the assessment, by the human reviewer, of the ICSR is required further comprises:

calculating, by the drug-adverse event causality evaluation engine, a sum of a weighted readability value and a weighted confidence value of the ICSR.

5. The method of claim 1, wherein determining whether or not the assessment, by the human reviewer, of the ICSR is required further comprises:

utilizing, by the drug-adverse event causality evaluation engine, a first threshold to determine whether the assessment, by the human reviewer, of the ICSR is required; and utilizing, by the drug-adverse event causality evaluation engine, one or more other thresholds to determine a level of expertise of the human reviewer required to review the ICSR in response to the assessment by the human reviewer of the ICSR being required.

6. The method of claim 1, wherein the cognitive system is a pharmacovigilance cognitive medical system.

7. The method of claim 1, where analyzing the unstructured natural language text within the ICSR, the drug-adverse event causality evaluation engine looks at one or more of word length, sentence length, average number of words per sentence, number of syllables for each word, or average number of syllables per word to compute the readability value of the ICSR.

8. The method of claim 1, wherein normalizing the probability value utilizes either an isotonic regression and a validation set or monotonic regression and the validation dataset to ensure that the probability value out of 100 outputs for a true confidence value.

9. A computer program product comprising a computer readable storage medium having a computer readable program stored therein, wherein the computer readable program, when executed on a data processing system, causes the data processing system to implement a drug-adverse event causality evaluation engine to identify human resource selections based on a readability of unstructured natural language text within an individual case safety report (ICSR) and a confidence value of the ICSR, and further causes the data processing system to:

receive, by the drug-adverse event causality evaluation engine, the ICSR from a cognitive system;

analyze, by the drug-adverse event causality evaluation engine, the unstructured natural language text within the ICSR to determine a readability value of the ICSR;

normalize, by the drug-adverse event causality evaluation engine, a probability value indicating a level of confidence of an algorithm within the cognitive system that generated the ICSR thereby generating the confidence value of the ICSR;

determine, by the drug-adverse event causality evaluation engine, whether or not an assessment, by a human reviewer, of the ICSR is required based on a combination of the readability value of the ICSR and the confidence value of the ICSR by using regression techniques to learn a set of weights that are used to weight the readability value of the ICSR and the confidence value of the ICSR wherein the set of weights for the readability value of the ICSR and the confidence value of the ICSR meet a defined constraint and wherein the set of weights are adjusted based on a training of the drug-adverse event causality engine so as to adhere to the defined constraint; and by process, by the drug-adverse event causality evaluation engine, the ICSR based on the determination of whether the human reviewer assessment is required.

10. The computer program product of claim 9, wherein the computer readable program to determine whether or not the assessment, by the human reviewer, of the ICSR is required further causes the data processing system to:

determine, by the drug-adverse event causality evaluation engine, a level of expertise of the human reviewer required to review the ICSR based on the readability value and the confidence value of the ICSR.

11. The computer program product of claim 9, wherein the computer readable program to determine whether or not the assessment, by the human reviewer, of the ICSR is required further causes the data processing system to:

determine, by the drug-adverse event causality evaluation engine, a number of human reviewers required to review the ICSR based on the readability value and the confidence value of the ICSR.

12. The computer program product of claim 9, wherein the computer readable program to determine whether or not the assessment, by the human reviewer, of the ICSR is required further causes the data processing system to:
calculate, by the drug-adverse event causality evaluation engine, a sum of a weighted readability value and a weighted confidence value of the ICSR.

13. The computer program product of claim 9, wherein the computer readable program to determine whether or not the assessment, by the human reviewer, of the ICSR is required further causes the data processing system to:
utilize, by the drug-adverse event causality evaluation engine, a first threshold to determine whether the assessment, by the human reviewer, of the ICSR is required; and
utilize, by the drug-adverse event causality evaluation engine, one or more other thresholds to determine a level of expertise of the human reviewer required to review the ICSR in response to the assessment by the human reviewer of the ICSR being required.

14. The computer program product of claim 9, wherein the cognitive system is a pharmacovigilance cognitive medical system.

15. A data processing system comprising:
at least one processor; and
at least one memory coupled to the at least one processor, wherein the at least one memory comprises instructions which, when executed by the at least one processor, cause the at least one processor to implement a drug-adverse event causality evaluation engine to identify human resource selections based on a readability of unstructured natural language text within an individual case safety report (ICSR) and a confidence value of the ICSR, and further cause the at least one processor to:
receive, by the drug-adverse event causality evaluation engine, the ICSR from a cognitive system;
analyze, by the drug-adverse event causality evaluation engine, the unstructured natural language text within the ICSR to determine a readability value of the ICSR;
normalize, by the drug-adverse event causality evaluation engine, a probability value indicating a level of confidence of an algorithm within the cognitive system that generated the ICSR thereby generating the confidence value of the ICSR;
determine, by the drug-adverse event causality evaluation engine, whether or not an assessment, by a human reviewer, of the ICSR is required based on a combination of the readability value of the ICSR and the confidence value of the ICSR by using regression techniques to learn a set of weights that are used to weight the readability value of the ICSR and the confidence value of the ICSR, wherein the set of weights for the readability value of the ICSR and the confidence value of the ICSR meet a defined constraint and wherein the set of weights are adjusted based on a training of the drug-adverse event causality engine so as to adhere to the defined constraint; and
process, by the drug-adverse event causality evaluation engine, the ICSR based on the determination of whether the human reviewer assessment is required.

16. The data processing system of claim 15, wherein the instructions to determine whether or not the assessment, by the human reviewer, of the ICSR is required further cause the at least one processor to:
determine, by the drug-adverse event causality evaluation engine, a level of expertise of the human reviewer required to review the ICSR based on the readability value and the confidence value of the ICSR.

17. The data processing system of claim 15, wherein the instructions to determine whether or not the assessment, by the human reviewer, of the ICSR is required further cause the at least one processor to:
determine, by the drug-adverse event causality evaluation engine, a number of human reviewers required to review the ICSR based on the readability value and the confidence value of the ICSR.

18. The data processing system of claim 15, wherein the instructions to determine whether or not the assessment, by the human reviewer, of the ICSR is required further cause the at least one processor to:
calculate, by the drug-adverse event causality evaluation engine, a sum of a weighted readability value and a weighted confidence value of the ICSR.

19. The data processing system of claim 15, wherein the instructions to determine whether or not the assessment, by the human reviewer, of the ICSR is required further cause the at least one processor to:
utilize, by the drug-adverse event causality evaluation engine, a first threshold to determine whether the assessment, by the human reviewer, of the ICSR is required; and
utilize, by the drug-adverse event causality evaluation engine, one or more other thresholds to determine a level of expertise of the human reviewer required to review the ICSR in response to the assessment by the human reviewer of the ICSR being required.

* * * * *